US011234652B2

(12) United States Patent
Felix et al.

(10) Patent No.: US 11,234,652 B2
(45) Date of Patent: Feb. 1, 2022

(54) METHOD FOR LOW NOISE BIOPOTENTIAL SIGNAL MEASUREMENT

(71) Applicants: Jason Felix, Vashon, WA (US); Leslie A Chertok, Vashon, WA (US); Vandana Verma, Mountain View, CA (US)

(72) Inventors: Jason Felix, Vashon, WA (US); Leslie A Chertok, Vashon, WA (US); Vandana Verma, Mountain View, CA (US)

(73) Assignee: BIOPAUSE, Vashon, WA (US)

(*) Notice: Subject to any disclaimer, the term of this patent is extended or adjusted under 35 U.S.C. 154(b) by 0 days.

(21) Appl. No.: 16/297,053

(22) Filed: Mar. 8, 2019

(65) Prior Publication Data

US 2019/0380654 A1 Dec. 19, 2019

Related U.S. Application Data

(60) Provisional application No. 62/640,763, filed on Mar. 9, 2018.

(51) Int. Cl.
*A61B 5/00* (2006.01)
*A61B 5/24* (2021.01)
*A61B 5/25* (2021.01)
*A61B 5/296* (2021.01)

(52) U.S. Cl.
CPC .............. *A61B 5/7203* (2013.01); *A61B 5/24* (2021.01); *A61B 5/2415* (2021.01); *A61B 5/25* (2021.01); *A61B 5/296* (2021.01); *A61B 5/6822* (2013.01); *A61B 5/6824* (2013.01);
(Continued)

(58) Field of Classification Search
CPC .............. A61B 5/7203; A61B 5/04001; A61B 5/04002; A61B 5/0408; A61B 5/0492; A61B 5/6822; A61B 5/6824; A61B 5/6831; A61B 2503/40; A61B 2562/0209
See application file for complete search history.

(56) References Cited

U.S. PATENT DOCUMENTS

| 230,243 A | 7/1880 | Crompton |
|---|---|---|
| 4,170,227 A | 10/1979 | Feldman |
| 5,336,242 A | 8/1994 | Zadeh |

(Continued)

OTHER PUBLICATIONS

Kajikawa, Yoshinobu et al. Recent Advances on Active Noise control:open issues and innovative applications. APSIPA Transactions on Signal and Information Processing. Cambridge University Press, UK. SIP (2012), vol. 1, e3, p. 1-21.
(Continued)

*Primary Examiner* — Michael W Kahelin

(57) ABSTRACT

This application relates to physiological monitoring typically for health and fitness purposes. Specifically, this application targets health and fitness monitors that require low noise acquisition of low amplitude biopotential signals. The method herein allows measurement and acquisition of biopotential signals that are normally too small to resolve due to the noise floor limitations of modern low noise amplifiers. Examples of applications that this method enables include monitoring devices located in far proximity from the location in which a biopotential signal originates, such as a wrist worn cardiac monitor, or a device that needs to sense low amplitude, fine muscle or nerve activity in a localized region.

8 Claims, 4 Drawing Sheets

(52) U.S. Cl.
CPC ........ *A61B 5/6831* (2013.01); *A61B 2503/40* (2013.01); *A61B 2562/0209* (2013.01)

(56) References Cited

U.S. PATENT DOCUMENTS

| | | | |
|---|---|---|---|
| 5,704,365 | A | 1/1998 | Albrecht |
| 5,939,724 | A | 8/1999 | Eisen |
| 5,983,127 | A | 11/1999 | dePinto |
| 7,018,338 | B2 | 3/2006 | Vetter |
| 7,485,095 | B2 | 2/2009 | Shusterman |
| 7,555,335 | B2 | 6/2009 | Kamath |
| 7,643,153 | B2 | 1/2010 | de Boer |
| 7,863,977 | B1 * | 1/2011 | Xiang .................. A61B 5/0428 330/69 |
| 2014/0358024 | A1 * | 12/2014 | Nelson ............... A61N 1/36139 600/544 |
| 2015/0109007 | A1 * | 4/2015 | Townsend .............. G01R 1/203 324/692 |
| 2017/0173262 | A1 * | 6/2017 | Veltz ..................... G16H 20/17 |

OTHER PUBLICATIONS

Changgui Lin, Design of RF CMOS Low Noise Amplifiers: Gain-Boosted Common-Gate Topologies, Noise Analysis, and On-Chip Differential Inductor Modeling. Lambert Academic Publishing (2010).

* cited by examiner

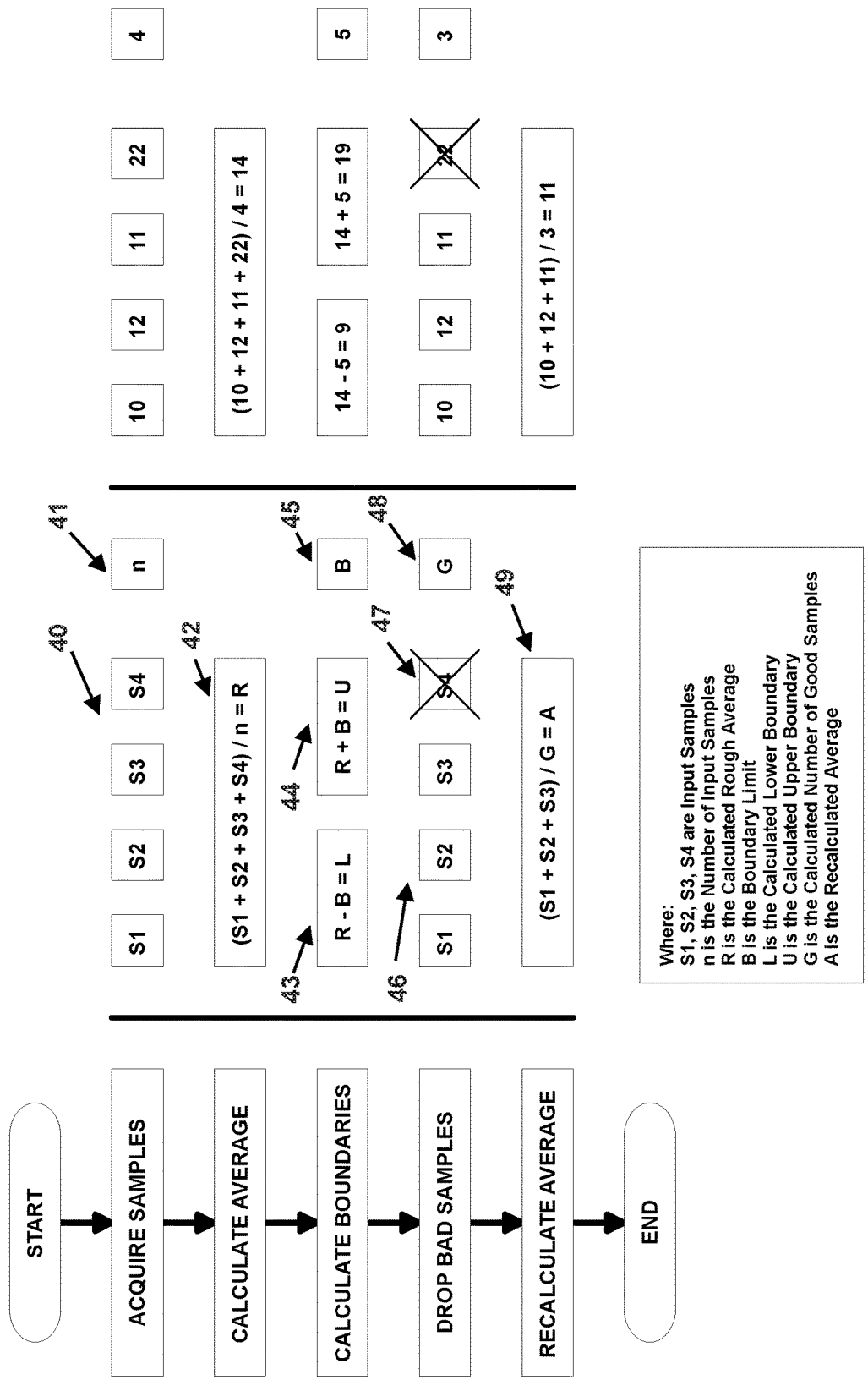

METHOD FOR LOW NOISE BIOPOTENTIAL SIGNAL MEASUREMENT

CROSS-REFERENCE TO RELATED APPLICATION

This non-provisional patent application claims priority under 35 U.S.C. § 119(e) to U.S. Provisional Patent Application No. 62/640,763 filed Mar. 9, 2018.

FIELD

This application relates to physiological monitoring typically for health and fitness purposes. Specifically, this application targets health and fitness monitors that require low noise acquisition of low amplitude biopotential signals. The method herein allows measurement and acquisition of biopotential signals that are normally too small to resolve due to the noise floor limitations of modern low noise amplifiers. Examples of applications that this method enables include monitoring devices located in far proximity from the location in which a biopotential signal originates, such as a wrist worn cardiac monitor, or a device that needs to sense low amplitude, fine muscle or nerve activity in a localized region.

BACKGROUND

The electrical signals within a body can be used to control, interact with and monitor most every aspect of the physical state of a mammal. Electrical signals in an intra-organism nervous system control almost every aspect of the voluntary and involuntary systems. Even what a mammal perceives consciously and unconsciously are driven by electrical signals conducted within the organism. From emotional state to communications relating to seeing, hearing, smelling, tasting, touching or sight, and regulation of involuntary systems, biological systems are largely a complex electrochemical signal delivery and processing networks.

Most of the electrical signals within an organism are of such low amplitude that modern monitoring and amplification technology is not capable of allowing observation of the relevant signals due to limitations in the noise floor of even the best low noise amplifier designs. Some monitoring and acquisition of signals may be enabled through direct physical connection to nerve fibers and tissues, however this is a highly invasive procedure and has limited application in a practical, ambulatory setting.

Invasive monitoring techniques can include catheterization, where a flexible tube with electrodes is inserted into the heart through the groin, or needle electrodes that pierce the dermal layer and are inserted into direct contact with the tissue that is to be observed. If a monitoring device were to contain an amplifier with a sufficiently low noise floor, increased positional freedom would be obtained and less invasive monitoring options would become viable. An application that would be enabled by a suitable low noise amplifier would include dermally connected electrodes that could receive diagnostically equivalent biopotential signals to invasive catheters or other subcutaneous biopotential pickups.

Some electrical signals within an organism are large enough to be observed with modern low noise amplifier designs, such as the differential biopotential voltages generated by the large cardiac muscles. Even so, limitations in the noise floor of modern amplifier designs only allow the observation of the larger cardiac muscles and nervous system impulses even with localized dermal pickup points in close proximity to their source. Finer movements of the musculatures are not able to be monitored, sometimes even with very invasive and positionally localized pickup locations due to limitations in the noise floor of amplifiers. The smaller signals are electrically present, and able to be processed by electrochemical systems within the body, however modern amplifier technology is limited by having a noise floor that is above the amplitude levels of the finer, low amplitude signals. Thus in practice, the finer muscle movements and nerve impulses are functionally invisible to modern monitoring devices.

The lowest noise cardiac monitor every created to date is the Cardiac Science mySense Heart device. It advertises an exceptionally low noise floor of 2.5 uV, revealing some of the finer and more important cardiac muscle actions represented by low amplitude waves (such as the p-wave). Even with this industry leading low noise floor, smaller wavelets within the cardiac rhythm are obscured to a point where they are not able to be monitored or recorded.

Limitations with modern amplifier technologies require that monitoring devices are located close to the muscles, organs or tissues generating the stimulus to be monitored for reception of fine muscle movements. Even with a very low noise floor, cardiac monitors such as the Cardiac Science mySense Heart must have sensing electrodes located somewhere in the trunk of the body, and are unsuitable to enable monitoring in more comfortable and accessible locations such as the wrist, forearm or legs.

In applications involving animals, the issues are similar, as electrical pickups (most commonly dermal or needle electrodes) must be placed near the organs being monitored (such as the cardiac organs). A sufficiently low noise floor amplifier would allow reliable cardiac and biopotential monitoring in convenient and accessible places such as the neck or for the system to be self contained within a single limb.

Although rough cardiac monitoring can be accomplished on the wrist using photoplethysmographic sensing technologies, that style of monitoring is power intensive and inaccurate when compared with differential voltage based monitoring of the electrical impulses generated by the cardiac muscles and their connected tissue. With current technology, limitations in the noise floor of amplifiers does not allow cardiac signals to be differentiated from noise using differential voltage sensing electrodes in the wrist or other locations located outside the trunk of the body.

A very small subset of electrical signals within the body can be monitored due to limitations in the noise floor of current amplifiers, even though the typically unmonitorable subset of signals can provide a wealth of information related to the health state of various organs and muscles within the body.

A low noise amplification method is needed to allow the monitoring of lower amplitude signals. This will allow finer grained monitoring of smaller muscles, tissues, nerves and other electrical signals as well as allow freedom of placement of the monitoring device for larger amplitude signals.

The noise floor of modern signal amplification and monitoring systems is limited by the random thermal noise generated by active and passive elements within the amplifier design as well as in the acquisition subsystems. In one example, the OPA330 made by Texas Instruments has a datasheet specified noise floor of 1.1 uVp-p. Typically, multiple copies of these or similar amplifiers are used in series in a design to arrive at a desired system result. Each amplification stage within a design introduces random thermal noises as electrons randomly bleedoff from elements within the semiconductor. In series, typically multiple amplification stages multiply the amount of noise in the system together.

In one example, common to most ECG systems, a low gain instrumentation amplifier is connected to a high gain amplifier. The noise present in the first stage is multiplied by the gain of the second stage. The actual noise of the amplification element is larger than the rating of the individual amplifiers.

The main advantage of the noise within a circuit element being random, is that when multiple amplifications are performed in parallel and their results combined, the overall noise floor is reduced. In a parallel summing amplifier configuration the noise will decrease by $\sqrt{2}*n/n$ where n is the number of parallel stages that are being summed together. With a sufficient number of parallel stages, the noise floor of the system can be reduced beyond the noise floor of the individual components that make up the amplification elements.

Summing amplifiers as discussed in the paragraph above are nothing new, however, the use of them in an application that allows the capture of biopotential signals that are currently believed to be unmonitorable, has never been done and is new. Signals in which additional detail can allow more fine discernment of physiological state, and enable the monitoring of signals that are located in distant proximity to their generating sources is new and unique. Furthermore, the intelligent selection of parallel channels or banks of parallel channels for decreased overall system noise before final summation and calculation of a sample is also a new technique that can be used to reduce noise in a system beyond what is practiced in the art at this time.

The application of this method can enable a variety of health and fitness, or even medical monitoring devices that measure differential voltages that propagate throughout the body when various muscles, organs and tissues contract and relax. Contractions and relaxations that cause large motions or do more work tend to generate high amplitude differential potentials which can be sensed easily in close proximity to where the muscles or organs are located. Biopotential voltages can be sensed in a variety of locations and through a variety of electrical pickup devices. The pickups are most commonly electrodes that adhere to the skin, or metallic plates held on by a band, but can also be in the form of catheters inserted into the body, or even needles that penetrate the dermal layer.

Various pickup locations and configurations provide insight into the actuation and relaxation of muscles, organs and tissues throughout the body. As the cardiac wavefront is generated from the contraction and relaxation of the cardiac muscles, the wavefront propagates throughout the trunk of the body, and certain parts of the waveform become more pronounced, while other portions decrease in amplitude. Typically the high frequency and high amplitude components of the cardiac rhythm signal become more pronounced while the low frequency, low amplitude biopotentials become obscured. As the wavefront enters the limbs it rapidly loses amplitude.

A cardiac waveform is typically divided into segments that represent various biopotential voltages generated within the heart. Typical wavelets within the heart rhythm known in the art are referred to as P, Q, R, S, T, U and H. Wavelets such as P, Q, S, T, U are low frequency and often low amplitude even near the muscles that generate them. Wavelets such as R wave are high frequency and easy to measure from most places within an organism. The H wavelet is the highest frequency wavelet and the lowest amplitude of all the cardiac wavelets that are currently known in the art, it is only measurable via catheters inserted in the heart, or with special software that averages thousands of heart beats from dermal electrode pickups.

As electrodes are placed nearer to the segments of the cardiac muscles and nerves that generate the biopotential signals, the amplitude of the biopotential signals tend to decrease as the measurements become more localized and the cardiac wavefront is less developed. Intra-electrode spacing is chosen to provide a balance between specificity of measurement and the ability to observe a signal without unacceptable decreases in amplitude that would obscure the signal.

The absolute signal to noise ratio increases as proximity to the muscles that generate the wavelet decreases. Thus, even though the overall amplitude in some cases is lower, sensing of fine muscle movements is possible as proximity to their generating source increases assuming the monitoring device has a low enough noise floor that it is able to resolve to fine, low amplitude signals.

Modern sensing technology is not able to resolve the smaller, more localized signals because of noise inherent with traditional amplifier technology, nor is it able to sense from locations on the extremities such as the wrist due to limitations in noise floor levels.

A further need remains for a signal acquisition method that is able to sense smaller amplitude signals, unobscured by an amplifier noise floor limitation that would enable freedom of the monitoring location (such as on the wrist on humans or neck for quadruped animals), enable small intra-electrode spacing for device size and comfort, and the ability to sense diagnostically important wavelets that are very difficult to observe from the dermal layers such as the U cardiac wavelet.

SUMMARY

Low amplitude, low noise biopotential acquisition may be enabled through a method of parallel sensing with optional parallel element selection. The parallel configuration of the sensing elements is able remove otherwise unfilterable random thermal noise from biopotential measurements which is currently inherent in all biopotential amplifiers. Parallel element selection masks signals that have excessive noise content, thus further decreasing the noise content found in the output of the system beyond the noise floor of the individual components. For simplicity and efficiency in implementation, a combination of both parallel amplification and sensing elements, plus intelligent selection can be combined.

In one embodiment, a noisy subcircuit of a biopotential amplifier is duplicated. The output of the noisy subcircuit is averaged or summed with two or more identical, duplicate subcircuits using a summing amplifier. Since the output of each identical subcircuit contains random noise, the averaging action of the subcircuits will decrease the effective noise floor by $\sqrt{2}*n/n$ where n is the number of parallel stages.

In another embodiment multiple, identical biopotential measurement channels are connected to a common pickup device such as an electrode. Their output is fed into separate channels of a series of analog to digital converters hosted on a microcontroller, FPGA, CPLD or similar controlling device. An average of all inputs is taken to determine the mean biopotential measurement and an out of bounds threshold is set to determine which channels have valid data. If a channel's biopotential measurement exceeds the out of bounds threshold, that channel's measurement would be excluded from the final average biopotential measurement, which would further decrease the overall noise level of the biopotential measurement.

In another embodiment, a hybrid technique of using multiple channels of multiple parallel elements summed together and then fed into multiple analog to digital converters. This technique can be used to reduce design complexity and implementation costs by only duplicating, then averaging or summing the noisiest elements.

The noise reduction method is especially suited to small biopotential monitors that are located in regions with low signal levels such as extremities, or where localized sensing of specific musculatures is desired. The benefits of the improved noise reduction sensing method enables the creation of smaller, more accurate wrist worn health and fitness monitors, and devices that are more convenient to be worn by non-human mammals. The method also enabled biopotential sensors with very short intra-electrode spacing and monitors that are able to observe small musculatures, tissues and nerve signals that are currently unmonitorable using modern amplifier technology.

The method illustrated above is not limited to the detail shown above or described in the accompanying text. As those of skill in the art will understand, a suitable parallel element sensing system can be constructed with varying subsections of subcircuits duplicated and summed or averaged together. Typically the subcircuit sections with the highest random noise contributions would be duplicated and/or masked using intelligent selection, while the subsections with low noise contributions would be implemented, in serial with the final result being summed or averaged and optionally digitized.

BRIEF DESCRIPTION OF THE DRAWINGS

FIG. 6 is a detailed diagram showing a method of masking excessively noisy samples from multiple ADC (analog to digital converter) inputs including worked examples for calculating an out of bounds condition for masking noisy samples. The column on the left is the flow diagram of FIG. 5, the middle column is a mathematical model of the flow diagram, and the column on the right is a worked example showing a sample calculation for a given set of example inputs.

DETAILED DESCRIPTION

Figure 1:
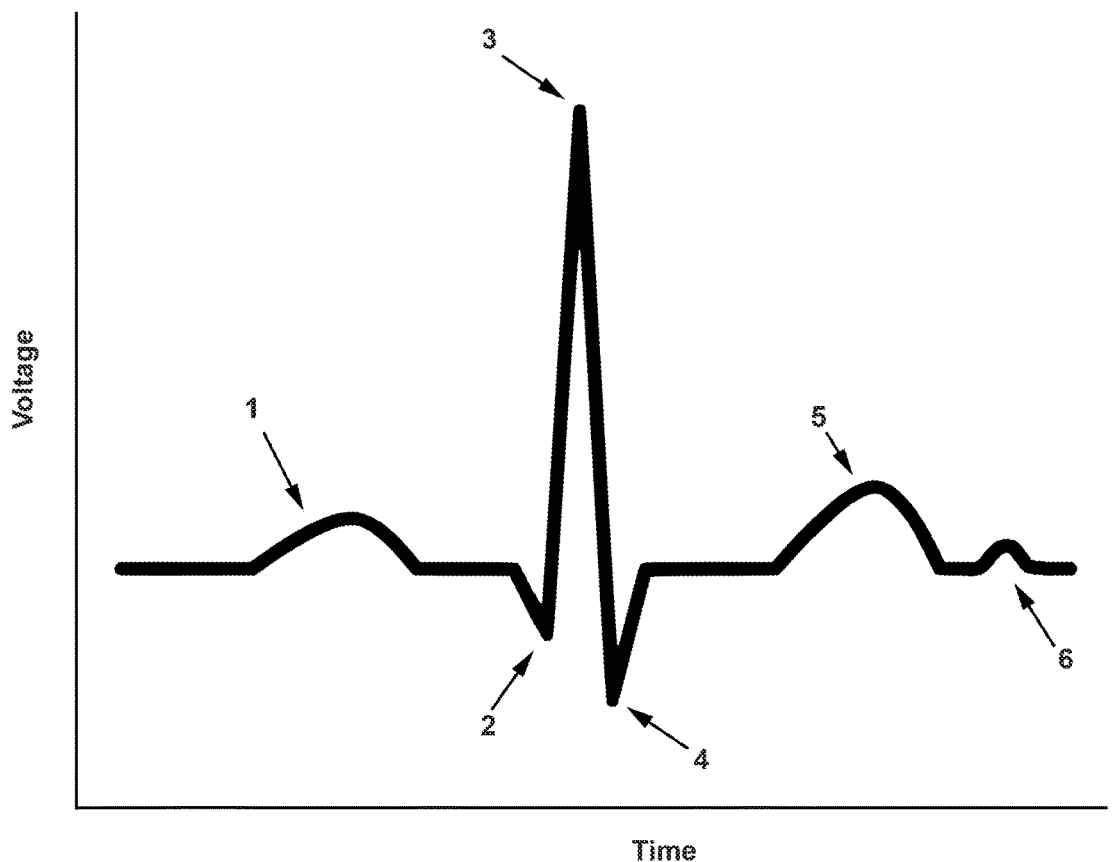
FIG. 1 is a diagram of a cardiac biopotential differential voltage plot of one heart beat.
Figure 2:
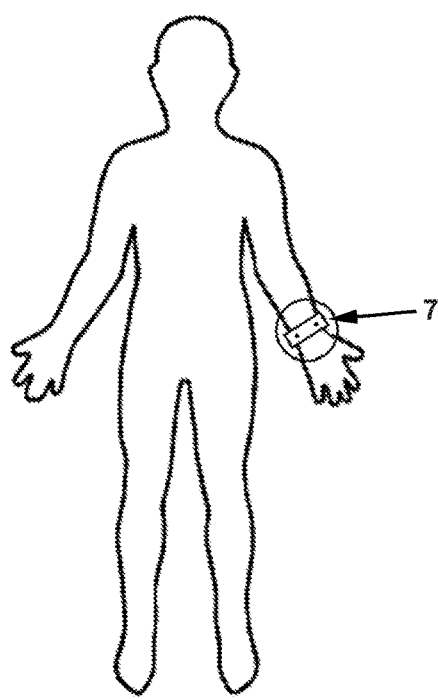
FIG. 2 is a perspective view showing a wrist worn health and fitness monitor with two electrode connection points.

A method for low noise reception of cardiac biopotential signals can be provided by attaching to the organism being monitored. FIG. 2. is a diagram showing by way of example, 7 a wrist worn electrode array with two electrical pickup points. A small biopotential voltage develops across the two electrodes when the cardiac muscles or connected tissues contract or relax. Although only this one example is specified, given a sensitive enough amplification method, the electrodes can be attached to virtually any part of the organism to receive the cardiac wavefront or similar low amplitude biopotential signal.

Figure 3:
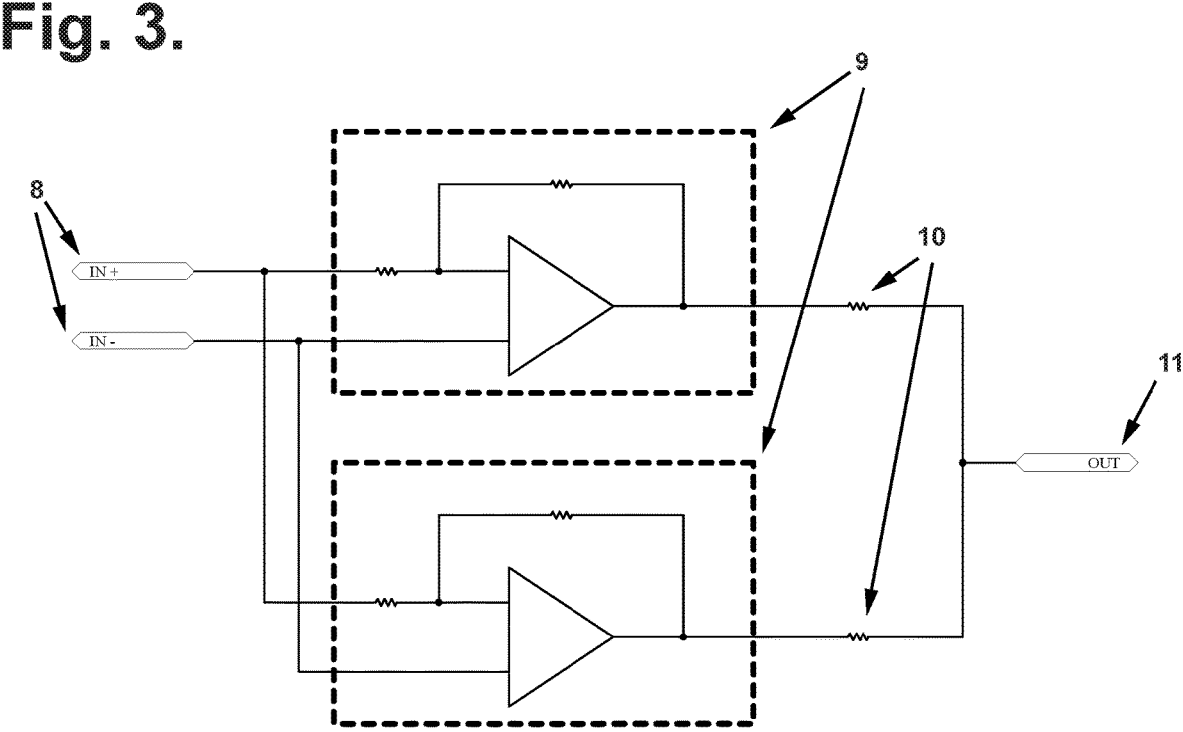
FIG. 3 is a functional block diagram showing the circuitry of a low noise, parallel two element amplifier.

In FIG. 3 the two electrical pickup points are attached to the two inputs 8 of a parallel, multiple element low noise amplifier. Each parallel element 9 performs a function, but during that process contributes random thermal noise to the overall signal. The output of the parallel elements are averaged or summed together. In this example they are averaged by means of a set of averaging resistors 10. The averaged output is provided by connection 11. Other averaging and summation methods are possible depending on the nature of the parallel elements that contribute random noise, such as direct connection, digitization and averaging or AC coupling thorough an array of capacitors or through a resistor, capacitor (RC) network.

Figure 4:
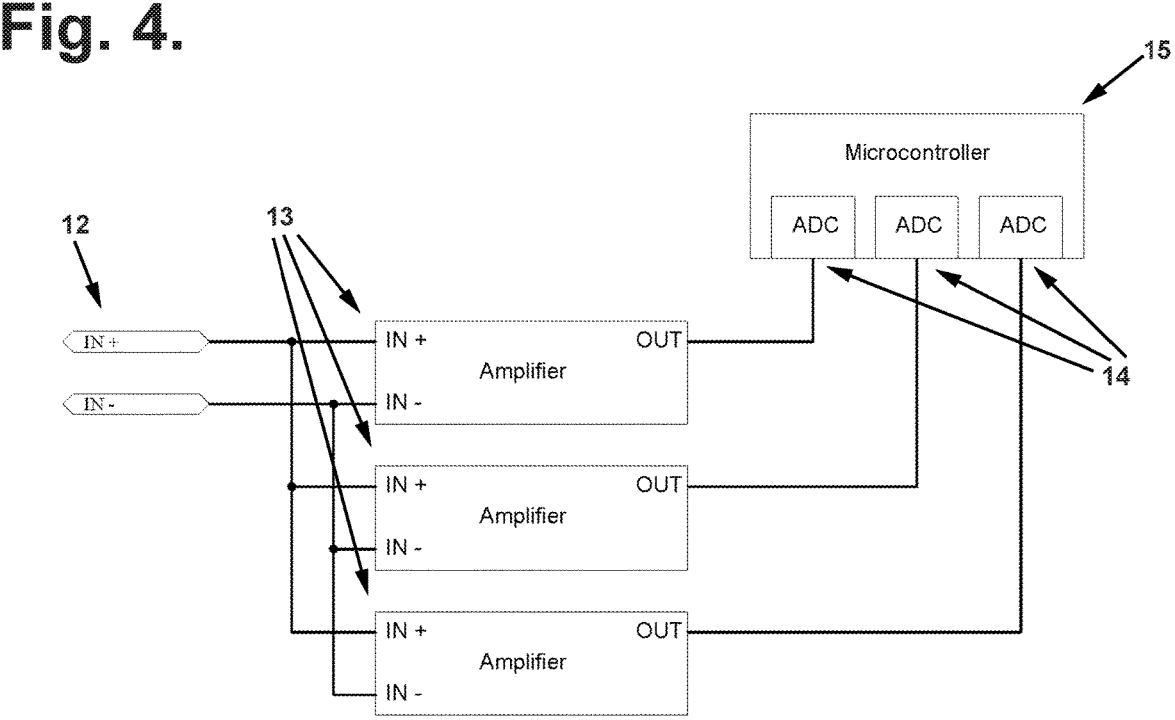
FIG. 4 is a functional block diagram showing the functional blocks of a low noise, parallel three element amplifier with microcontroller controlled sample collection and masking.

In another embodiment diagramed in FIG. 4 The two electrical pickup points are attached to the two inputs 12 of an array of parallel elements 13 (for illustrative purposes a set of amplifiers). The array of parallel elements 13 performs a function on the input, but also produces random noise as a byproduct of its operation. The output of the parallel elements is fed into a series of analog to digital converters (ADCs) 14 allowing a processing element 15, such as a microcontroller, access to digital representations of each parallel element 13 output 14.

Figure 5:
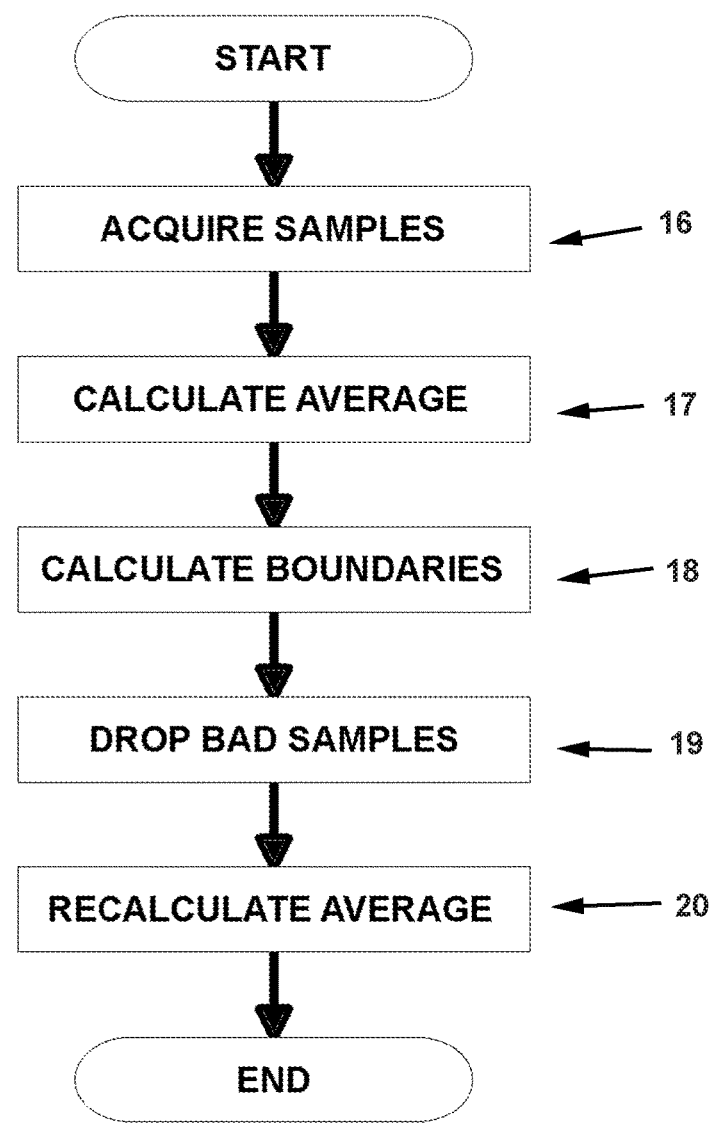
FIG. 5 is a flow diagram showing a method of masking excessively noisy samples from multiple ADC (analog to digital converter) inputs.

A microcontroller or suitable processing element 15 runs a program to eliminate out of bounds data that is received from the processing elements. In FIG. 5, a flow diagram is shown that is capable of eliminating outputs from the parallel element array that contain excessive error. In 16 an array of samples are acquired by the analog to digital converters 14. The average of the samples is calculated to determine a reasonable target value for the inputs. A variety of averaging methods are suitable such as, calculating the mean, median, mode, weighted average or other methods. The averaging method may also take into account previously known good data points from the last array of samples. Once a suitable average is found, upper and lower limits are calculated in function 18. Samples that exceed the limits established in 18 are removed from the data array 19 and the average is recalculated 20.

In the worked example diagramed in FIG. 6, four samples (S1, S2, S3 and S4) 40 from an array of four analog to digital converters 14 will be processed. The number of samples from the parallel ADC channels 14 are held in the variable n 41. A simple average 42 is calculated and stored in the variable R. A variable B 45 contains a threshold limit. In simple applications the limit could be a hard coded value determined by reasonably expected deviations in parallel ADC performance. In advanced applications, an adaptive or learning method could be used to inform the value of B. The lower limit L is calculated 43 by subtracting the rough average 42 from the boundary limit B 45. The upper limit U is calculated 44 by adding the rough average 42 to the boundary limit B 45.

The four input samples (S1, S2, S3 and S4) 40 are compared to the computed upper 44 and lower 43 limits. Samples exceeding the upper 44 and lower 43 limits are marked 47 and discarded from future calculations 49. In this example sample S4 47 was found to exceed the upper limit 44 U. The number of valid samples without the boundaries of the upper 44 and lower 43 limits is stored in variable G

48. A new average A is computed 49 which exclude raw samples that have been determined to exceed the boundary limit conditions.

In another embodiment a combination of parallel element blocks such as shown in FIG. 3 compromise the parallel elements as shown in FIG. 4 13 and are connected to a series of analog to digital converters 14 connected to or internal to a processing element 15. The program in FIG. 5 is then executed to get a low noise biopotential sample.

While the method has been shown and described as referenced, those skilled in the art will understand that changes in form and detail such as utilization of alternative parallel elements, alternative methods of averaging, alternative methods of discarding bad samples, externalization of microcontroller system components or an internalization of microcontroller system components may be made therein without departing from the intention of the invention.

The invention claimed is:

1. A system for measuring a biopotential signal comprising:
 a) two or more parallel amplifying and sensing channels that are configured to monitor the same signal source;
 b) two or more analog to digital converters arranged in a parallel configuration, each connected to one of the parallel amplifying and sensing channels, and configured to synchronously acquire a sample set of magnitude values; and
 c) a processing element configured to:
   i) average the synchronously acquired sample set,
   ii) calculate a set of one upper and one lower boundary from the average of the sample set, the upper boundary being the average of the sample set added to a predefined maximum deviation limit, the lower boundary being the average of the sample set subtracted from the maximum deviation limit,
   iii) calculate a second set of values containing the synchronously acquired sample set excluding any values that exceeded the calculated upper or lower boundaries,
   iv) calculate an average of the second set of values as an output value, and
   v) output the output value from the system.

2. The system of claim 1 wherein the system is configured to monitor electrical biopotential signals originating in the trunk of a body, wherein the measurement points are completely contained on a single limb.

3. The system of claim 1 wherein the system is configured to reside on a flexible band containing surface monitoring electrodes.

4. The system of claim 3 wherein the surface monitoring electrodes are comprised of smart fabric.

5. The system of claim 3 wherein the flexible band is configured to be worn on the wrist.

6. The system of claim 3 wherein the flexible band is configured to be worn on the neck.

7. The system of claim 3 when the flexible band is configured to be worn on a shoulder.

8. The system of claim 3 wherein the flexible band is configured to be worn by a non-human mammal.

* * * * *